(12) United States Patent
Raphael et al.

(10) Patent No.: US 9,791,368 B2
(45) Date of Patent: Oct. 17, 2017

(54) NANOSPLASMONIC IMAGING TECHNIQUE FOR THE SPATIO-TEMPORAL MAPPING OF SINGLE CELL SECRETIONS IN REAL TIME

(71) Applicants: Marc P. Raphael, Washington, DC (US); Joseph A. Christodoulides, Alexandria, VA (US); Jeff M. Byers, Fairfax Station, VA (US); James B. Delehanty, Washington, DC (US)

(72) Inventors: Marc P. Raphael, Washington, DC (US); Joseph A. Christodoulides, Alexandria, VA (US); Jeff M. Byers, Fairfax Station, VA (US); James B. Delehanty, Washington, DC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 796 days.

(21) Appl. No.: 14/207,927

(22) Filed: Mar. 13, 2014

(65) Prior Publication Data

US 2014/0273002 A1 Sep. 18, 2014

Related U.S. Application Data

(60) Provisional application No. 61/839,428, filed on Jun. 26, 2013, provisional application No. 61/778,652, filed on Mar. 13, 2013.

(51) Int. Cl.
*G01N 33/551* (2006.01)
*G01N 21/552* (2014.01)
(Continued)

(52) U.S. Cl.
CPC .......... *G01N 21/554* (2013.01); *G01N 21/59* (2013.01); *G01N 21/648* (2013.01);
(Continued)

(58) Field of Classification Search
None
See application file for complete search history.

(56) References Cited

U.S. PATENT DOCUMENTS

2010/0035335 A1* 2/2010 Lakowicz .......... G01N 21/6486
435/287.1
2014/0093977 A1* 4/2014 Raphael ........... G01N 33/54346
436/501
2014/0095100 A1* 4/2014 Raphael ............... G01N 21/276
702/104

OTHER PUBLICATIONS

Raphael et al, "A New Methodology for Quantitative LSPR Biosensing and Imaging", Anal. Chem. 2012, 84, 1367-1373, published Dec. 17, 2011.*
(Continued)

*Primary Examiner* — Chris L Chin
(74) *Attorney, Agent, or Firm* — US Naval Research Laboratory; Rebecca L. Forman

(57) ABSTRACT

A label-free method for the spatio-temporal mapping of protein secretions from individual cells in real time by using a chip for localized surface plasmon resonance (LSPR) imaging. The chip is a glass coverslip compatible for use in a standard microscope having at least one array of functionalized plasmonic nanostructures patterned onto it. After placing a cell on the chip, the secretions from the cell are spatially and temporally mapped using LSPR imaging. Transmitted light imaging and/or fluorescence imaging may be done simultaneously with the LSPR imaging.

6 Claims, 4 Drawing Sheets

(51) Int. Cl.
    *G01N 33/543*    (2006.01)
    *G01N 21/64*     (2006.01)
    *G01N 21/59*     (2006.01)
    *G01N 21/27*     (2006.01)

(52) U.S. Cl.
    CPC ... G01N 21/6458 (2013.01); G01N 33/54373 (2013.01); *G01N 21/274* (2013.01); *G01N 2021/6491* (2013.01)

(56) References Cited

OTHER PUBLICATIONS

Raphael et al, "Quantitative LSPR Imaging for Biosensing with Single Nanostructure Resolution", Biophysical Journal, vol. 104, Jan. 2013, 30-36.*

* cited by examiner

NANOSPLASMONIC IMAGING TECHNIQUE FOR THE SPATIO-TEMPORAL MAPPING OF SINGLE CELL SECRETIONS IN REAL TIME

PRIORITY CLAIM

The present application is a non-provisional application claiming the benefit of U.S. Provisional Application No. 61/778,652, filed on Mar. 13, 2013 by Marc P. Raphael et al., entitled "Nanoplasmonic Imaging Technique for the Spatio-Temporal Mapping of Single Cell Secretions in Real Time" and U.S. Provisional Application No. 61/839,428, filed on Jun. 26, 2013 by Marc P. Raphael et al., entitled "Silicon Backing Ring and Multiplexing Applications for LSPR Imaging." The entire contents of both are incorporated herein by reference.

BACKGROUND OF THE INVENTION

Field of the Invention

The present invention relates generally to paracrine signal measuring and, more specifically, to label-free mapping of single cell secretions in real time.

Description of the Prior Art

Paracrine signaling is a form of close-range communication between cells, typically mediated by the secretion of proteins. The types of proteins secreted as well as their spatial and temporal distributions give rise to a broad range of possible responses amongst the receiving cells, including cell migration and proliferation. Not surprisingly then, paracrine signaling is found to play a central role in a diverse range of processes such as wound healing, angiogenesis and immune response, which rely heavily on cell movement and division. The ability to map the spatio-temporal nature of individual cell secretions is thus foundational to understanding these processes.

There are, however, a number of roadblocks encountered in trying to measure paracrine signaling due to the proteins being both highly localized and external to the cell. While fluorescent fusion protein tags are now standard for tracking intracellular signaling, the approach is problematic for studying secreted proteins. First, the presence of a relatively large tag (27 kDa for GFP) may hamper the cell's ability to secrete the protein of interest. Second, even if the molecule and its fluorescent protein tag are successfully secreted, the result is a diffuse glow in the vicinity of the cell that is difficult to track quantitatively in space and time.

As a result, direct measurements of secreted proteins from individual cells are typically performed using techniques founded upon immunosandwich assays that either use fluorescent antibodies or colormetric enzymatic reactions. While in the past such measurements had time resolutions on the order of days, technological advances that couple immunosandwich assays with lithographically patterned microwells and microfluidics have enabled quantitative secretion monitoring with time resolutions on the order of hours. Such advances have exposed cyclical behaviors in the rates at which stimulated T cells secrete cytokines, and in a more general sense, have demonstrated how improving time resolutions can enhance the understanding of intercellular signaling. Improved temporal resolutions hold the promise of detecting the time for individual cells to begin secretion after external stimulation, correlating secretion rates with stages of the cell cycle and, as we show in the present invention, distinguishing burst-like secretions from those that are more steady state in nature. Immunosandwich-based assays are now capable of measuring hundreds or thousands of individual cells per experiment but their temporal resolution is limited by the introduction of the antibody probe which necessarily halts or ends the secretion study. A complimentary technique that focuses on a small number of cells but with higher spatial and temporal resolution promises to help complete the picture of close range cell-to-cell communication by bridging the time scale gap from seconds to days.

BRIEF SUMMARY OF THE INVENTION

The aforementioned problems are overcome in the present invention which provides a label-free method for the spatio-temporal mapping of protein secretions from individual cells in real time by using a chip for localized surface plasmon resonance (LSPR) imaging. The chip is a glass coverslip compatible for use in a standard microscope having at least one array of functionalized plasmonic nanostructures patterned onto it. After placing a cell on the chip, the secretions from the cell are spatially and temporally mapped using LSPR imaging. Transmitted light imaging and/or fluorescence imaging may be done simultaneously with the LSPR imaging.

The application of nanoplasmonic imaging to the study of extracellular signaling brings with it a number of advantages: (1) The protein secretions are measured in real-time with the frequency of time points limited only by the exposure time of the camera, typically 250-400 ms. (2) The Au plasmonic nanostructures are lithographically patterned onto standard glass coverslips enabling more traditional imaging techniques such as fluorescence and bright field imagery to be readily integrated into the experiments. Thus, morphological changes and intracellular fluorescent tags can be monitored simultaneously in real time. (3) The nanostructures are calibrated for the quantitative determination of secreted protein concentration as a function of time and space. (4) Arrays of Au nanostructures positioned sufficiently far away from the cells can be utilized as control arrays used to distinguish global variations in signal from localized cell secretions. (5) The technique is applicable to both adherent and non-adherent cell lines. (6) Unlike fluorescent probes. Au plasmonic nanostructures do not exhibit blinking or photobleaching, both of which are problematic in the previous methods described above.

There is currently no alternative method for the label-free and real time imaging of protein secretions from individual cells that integrates the standard glass coverslips widely used for cell imaging and culture. The label-free technique described herein enables secretion studies with time resolutions on the order of hundreds of milliseconds and without labeling, whereas the commercially available sandwich assay-based techniques have time resolutions on the order of hours or days and require fluorescent tags or enzyme-based colormetric probes.

These and other features and advantages of the invention, as well as the invention itself, will become better understood by reference to the following detailed description, appended claims, and accompanying drawings.

BRIEF DESCRIPTION OF THE DRAWINGS

FIG. 1($a$) shows the nanoplasmonic response of a c-myc functionalized array to 200 nM of commercial anti-c-myc in serum-free media, introduced microfluidically. The mean intensity of the array was calculated within a 9.5×9.5 µm region-of-interest centered about the array for each time point. The illustrations highlight two response regimes for the functionalized nanostructures, which are depicted as cylinders. In the lower regime, only a small fraction of available c-myc peptides (spheres) are bound with anti-c-myc (low fractional occupancy, f) while almost all are occupied in the upper regime (f→1). No cells were present in this experiment. FIG. 1(b) is an illustration of an antibody-secreting cell in registry with two nanoplasmonic arrays. The chip is loaded onto an inverted microscope and the fact that the majority of the substrate is transparent glass allows for live cell imaging using transmitted light and fluorescence microscopy in parallel with the LSPR-based imaging technique used to measure the secretions.

FIG. 2(a) is an overlay of LSPR and TL images with the cell visible next to Array A as a result of the TL illumination while the nanoplasmonic arrays are illuminated in LSPR mode. FIG. 2(b) shows normalized LSPR image intensity ($\hat{I}_{cell}$) of Arrays A-D. The distances from the center of the cell to the center of each array were 15.4 µm, 39.2 µm, 72.2 µm, and 106 µm for Arrays A, B, C and D, respectively. The $\hat{I}_{cell}$ values have been offset to be equal before the burst (t≤7800 s) so that the detection time and intensity of the burst at each array can be more readily compared. FIG. 2(c) shows the mean intensity of Array D, highlighting the end of the experiment at which 250 nM of commercial anti-c-myc was introduced for the purpose of normalizing the response of the arrays. FIG. 2(d) shows an overlay of LSPR and fluorescence images exposing portions of the cell membrane labeled with Lissamin Rhodamine B. Scale bar: 10 µm.

FIG. 3(a) is an overlay of transmitted light and LSPR images highlighting the location of the cell relative to 12 arrays. FIG. 3(b) shows the normalized LSPR responses of Arrays A, B and C ($\hat{I}_{cell}$) minus the average normalized response of the three control Arrays D, E and F ($\hat{I}_{control}$). The centers of Arrays A, B and C were located 11 µm, 23 µm and 35 µm, respectively, from the center of the cell. Arrays D, E and F were all located at least 65 µm from the center of the cell. FIG. 3(c) shows an overlay of the two images (LSPR, transmitted light) with a spatial map of secreted antibody concentrations as generated by finite element analysis. For the calculation, the simulated cell was 16 µm in diameter, had an adhesion spot of 5.5 µm and secreted antibodies uniformly at 1000 antibodies/s. The concentration scale has units of pM and the distance scale bar is 10 µm.

DETAILED DESCRIPTION OF THE INVENTION

Figure 1:
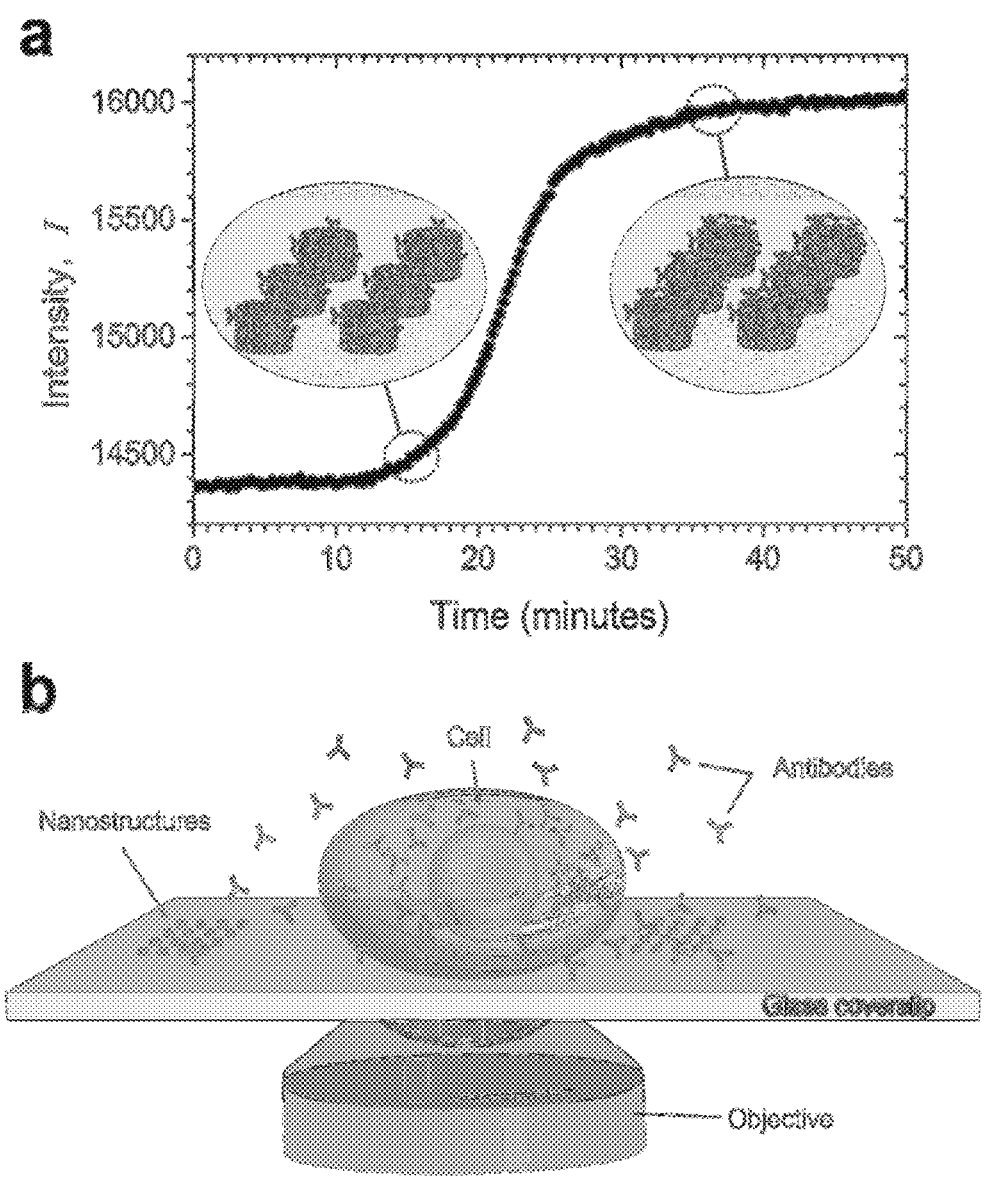
FIG. 1 shows principles of localized surface plasmon resonance (LSPR) imaging and the single cell secretion measurement.

The present invention provides a label-free approach based upon localized surface plasmon resonance (LSPR) imaging for the real-time measurement of protein secretions from individual cells. LSPR biosensing is founded upon the fact that the plasmonic resonance of a metallic nanostructure exhibits both a red shift and an increase in scattering intensity when analyte binding creates small perturbations in the local index of refraction. When imaged on a CCD camera these spectroscopic signatures are manifested as an increase in the brightness of the nanostructures (FIG. 1(a)) and can be quantified in terms of the fractional occupancy of surface bound receptors. In contrast to thin-film based surface plasmon resonance (SPR) approaches that require total internally reflected light for the excitation of the surface plasmons, nanoplasmonic resonances can be excited with visible light using the same optical configurations used in traditional wide-field microscopy setups (FIG. 1(b)).

The approach of the present invention has been validated by using LSPR imaging to spatially and temporally map the secretion of anti-c-myc antibodies from individual 9E10 hybridoma cells. Square arrays of gold nanostructures were patterned onto No. 1.5 glass coverslips using electron-beam nanolithography as described in Raphael et al., "A New Methodology for Quantitative LSPR Biosensing and Imaging," *Anal. Chem.*, 84, 1367-73 (2012), the entire contents of which is incorporated herein by reference. Each array (6×6 µm) consisted of 400 evenly spaced nanostructures separated by a pitch of 300 nm. The bases of the nanostructures were circular in cross section with diameters of 70±5 nm and the heights were 75±2 nm, which gave a plasmonic resonance peak centered about 625 nm when immersed in serum free cell culture media (SFM). The arrays were separated by 33 µm allowing for as many as 12 arrays to be incorporated into the field-of-view (FOV) when using a 63× microscope objective and as many as 35 arrays in the FOV when using a 40× objective. As such, 97% of the FOV was transparent glass, allowing for the cells on the glass portion to be viewed by traditional microscopy techniques such as fluorescence and transmitted light (TL) imaging. The remaining 3% was patterned with the Au nanostructure arrays and utilized for cell secretion measurements by LSPR imaging. In addition to the imagery, a beam splitter was placed before the CCD camera directing half the collected light to a fiber-optically coupled spectrometer. The fiber was aligned to collect spectra from the array closest to the cell and this spectral information was analyzed to determine the fractional occupancy of surface bound receptors. One data set was collected per minute comprising a combination of three images (LSPR, TL, and fluorescence) as well as the LSPR spectrum of the individual array.

The patterned coverslips were cleaned by hydrogen plasma ashing, and the gold nanostructures were functionalized with a two-component self-assembled monolayer (SAM) of thiols consisting of a 3:1 ratio of $SH-(CH_2)_8$-$EG_3$-OH(SPO) to $SH-(CH_2)_{11}$-$EG_3$-$NH_2$ (SPN). The SPN component was covalently conjugated with commercially available c-myc peptide. The functionalized chips were mounted onto a custom built microfluidic perfusion assembly for the introduction of fresh media and loaded onto a Zeiss Axio Observer inverted microscope. The assembly was enclosed within an incubation chamber regulated with 5% $CO_2$ and 98% humidity at 37° C.

Figure 2:
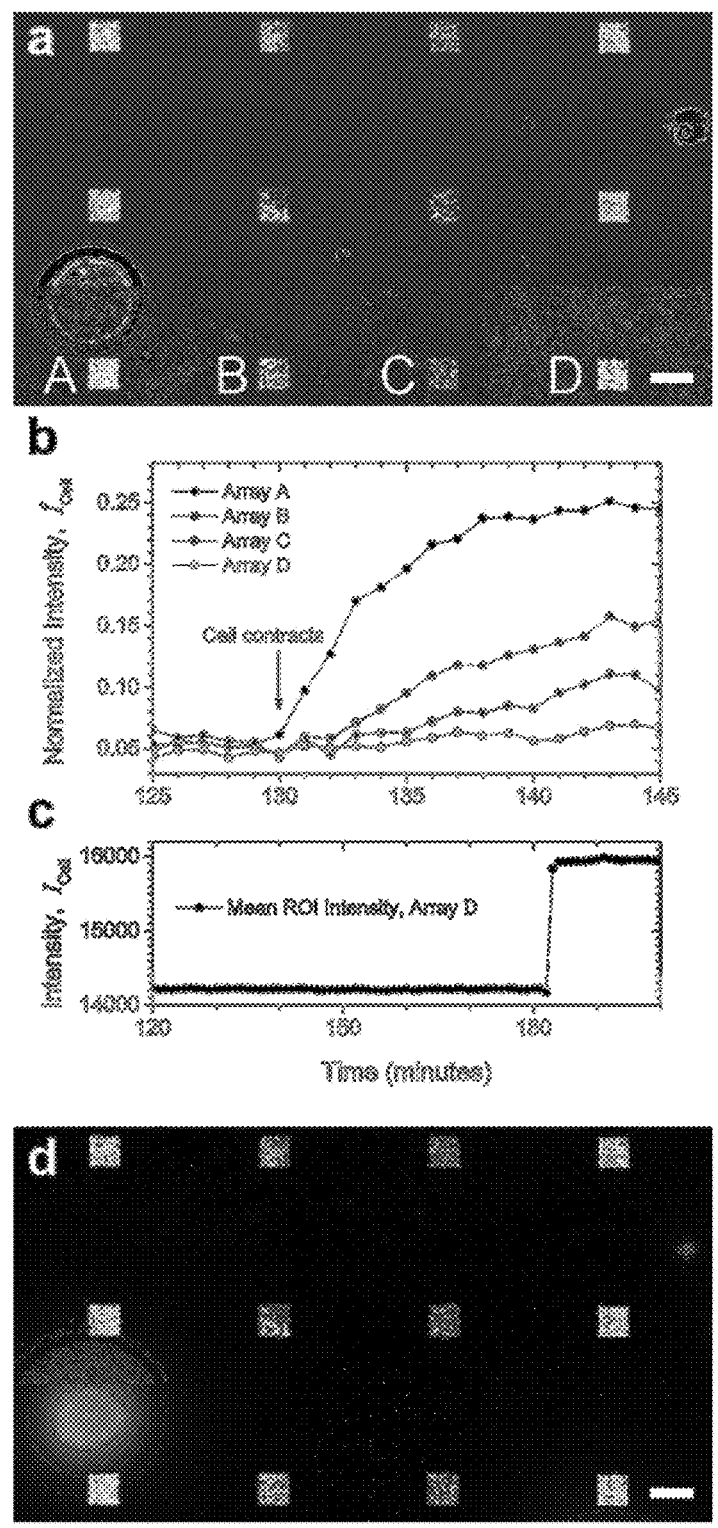
FIG. 2 shows secretion burst from a single cell.

In LSPR imaging mode, the arrays appear as bright squares on a dark background and only the portion of the cell adherent to the surface is visible, while in TL imaging the whole cell is visible and can be monitored for morphological changes (FIG. 2(a)). The one minute time resolution enabled the detection of bursts of secreted antibodies in LSPR imaging mode that otherwise would have gone undetected (FIG. 2(b)). In particular, at the 130 min mark of the experiment, the cell that had grown steadily to a diameter of 27 µm, contracted to 25 µm within the 1 minute time span between data points. Simultaneously, a sharp increase in the LSPR imaging signal was detected at the closest array (FIG. 2(b), Array A). Arrays B and C also detected a pulse, time delayed by 1 min and 3 min, respectively. The fact that the size and the slope of the signal decreased with increasing distance between cell and array is consistent with a pulsed wave of antibodies originating at the cell and diffusing outward. The diffusing wave was readily measured at arrays located at distances greater than 70 μm from the cell.

To account for variations in array intensity and dynamic range, the response of each array was individually normalized. The procedure consisted of introducing a saturating solution of commercial anti-c-myc antibodies (250 nM) at the end of the experiment (FIG. 2(c)). The mean intensity, I(t), within a 9.5×9.5 μm region-of-interest (ROI) centered about the array was then normalized at each time point, t, with the equation $\hat{I}(t)=[I(t)-I(t_o)]/[I(t_f)-I(t_o)]$, where $I(t_o)$ and $I(t_f)$ were the mean ROI intensities at the beginning of the experiment and after saturation, respectively.

Having both spatial and temporal information for the traveling waveform enabled the diffusion constant for the secreted antibodies to be estimated. Assuming a spherical emitter producing an outwardly propagating pulse of antibodies with a Gaussian concentration profile, the onset of the measured pulse was associated with the peak of the wave. In this limit, $D=r^2/6\cdot t$, where D is the diffusion constant, r is the distance from the center of the cell to the center of the array and t is the elapsed time from when the cell contracted. Analyzing all arrays in the FOV that detected the pulse, a range was obtained for D of $0.6\times10^{-7}$ cm$^2$/s$<$D$<5.5\times10^{-7}$ cm$^2$/s, which is consistent with the value of $4\times10^{-7}$ cm$^2$/s measured for IgG antibodies in buffered saline solution. The calculated range in D is in large part a result of the uncertainty in t, due to the 1 minute time resolution chosen for this experiment, as well as the association of the onset of the signal at the array with a particular feature of the Gaussian wave front. Nevertheless, the detection of a traveling wave of secreted proteins from a single cell and the ability to estimate D is illustrative of the general applicability of the present invention for the spatio-temporal mapping of paracrine signaling.

The cell plasma membrane was also labeled with the membrane-localizing dye Lissamin Rhodamine B, allowing for fluorescence-based imaging of membrane dynamics to be co-monitored with the LSPR and TL imaging (FIG. 2(d)). The ability to integrate fluorescence microscopy with LSPR imaging serves is an example of how the present invention enables well-established fluorescence methods for intracellular studies to be integrated with extracellular secretion investigations.

Figure 3:
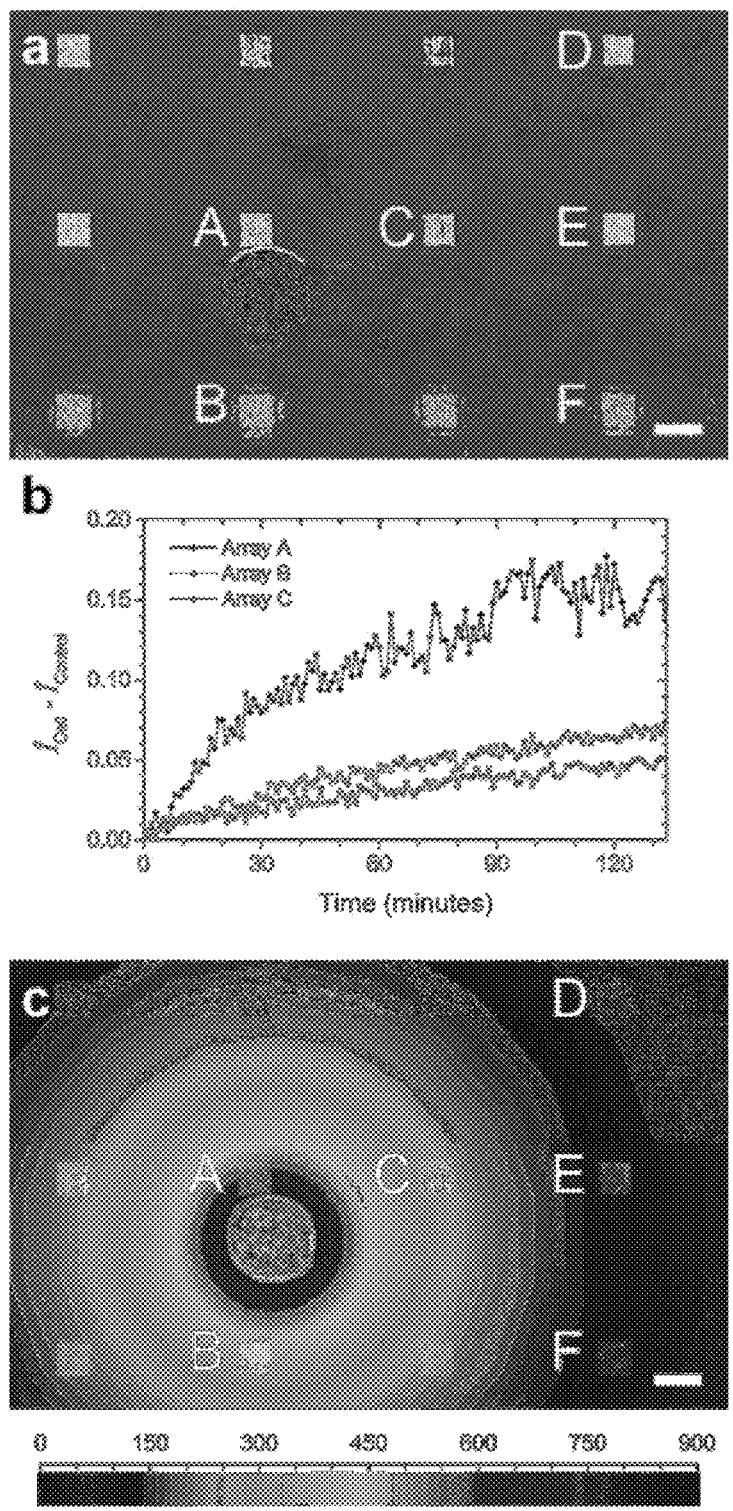
FIG. 3 shows a single cell secretion study.

The majority of cells studied exhibited continuous secretions over the course of the experiment as opposed to bursts (FIG. 3). The secretions from individual cells were isolated and quantified with arrays adjacent to the cell by normalizing the response of each array in the FOV as described above and then using the arrays located furthest from the cell as controls for background subtraction (FIG. 3(b)). Antibody secretions were observed within minutes of the start of the experiment and, as expected, the signal strength diminished with increasing distance between cell and array. In comparison to the secretive bursts that were detectable at distances greater than 70 μm from the cell, continuous secretions were detected at distances of 40 μm or less. Additional stochastic noise was often observed at the array closest to the cell (FIG. 3(b), Array A) due to changes in the cell's morphology that created variations in the scattered light at the edge of the cell. In the event that the cell spread over the surface during the experiment and made contact with the array, the scattered intensity from the plasmonic nanostructures increased measurably at the edge of the array adjacent to the cell, in marked contrast to the detection of secreted antibodies in which the array intensity increased uniformly.

The data analysis procedure for background subtraction was important for isolating continuous-type secretions from individual cells. The purpose of the background subtraction was to eliminate global changes in the signal that affect all arrays in the FOV over the course of the experiment, such as volumetric changes in the media composition, focus drift and variations in light source intensity. Arrays sufficiently distant from the cell were insensitive to its secretions and thus could serve as control arrays, conveniently integrated into the same experiment by the lithographic process. To help determine the minimum required separation distance between the cell and the control arrays, finite element analysis (FEA) was used to solve the diffusion equation in the vicinity of a model cell emitting antibodies at a constant rate. The secretion rate of 1000 antibodies/s used in the calculations was an experimentally-determined average based on bulk secretion rate studies of $4\times10^6$ cells. The FEA results (FIG. 3(c)) show that a separation between the cell and an array of greater than 65 μm reduces the secreted antibody concentration below the detection limit for the time scales under investigation (~100 pM). This agreed with the experimental observation that Arrays D, E, and F, located 70 μm, 68 μm, and 81 μm from the center of the cell, respectively, had normalized responses that were statistically indistinguishable over the course of the three hour experiment.

Figure 4:
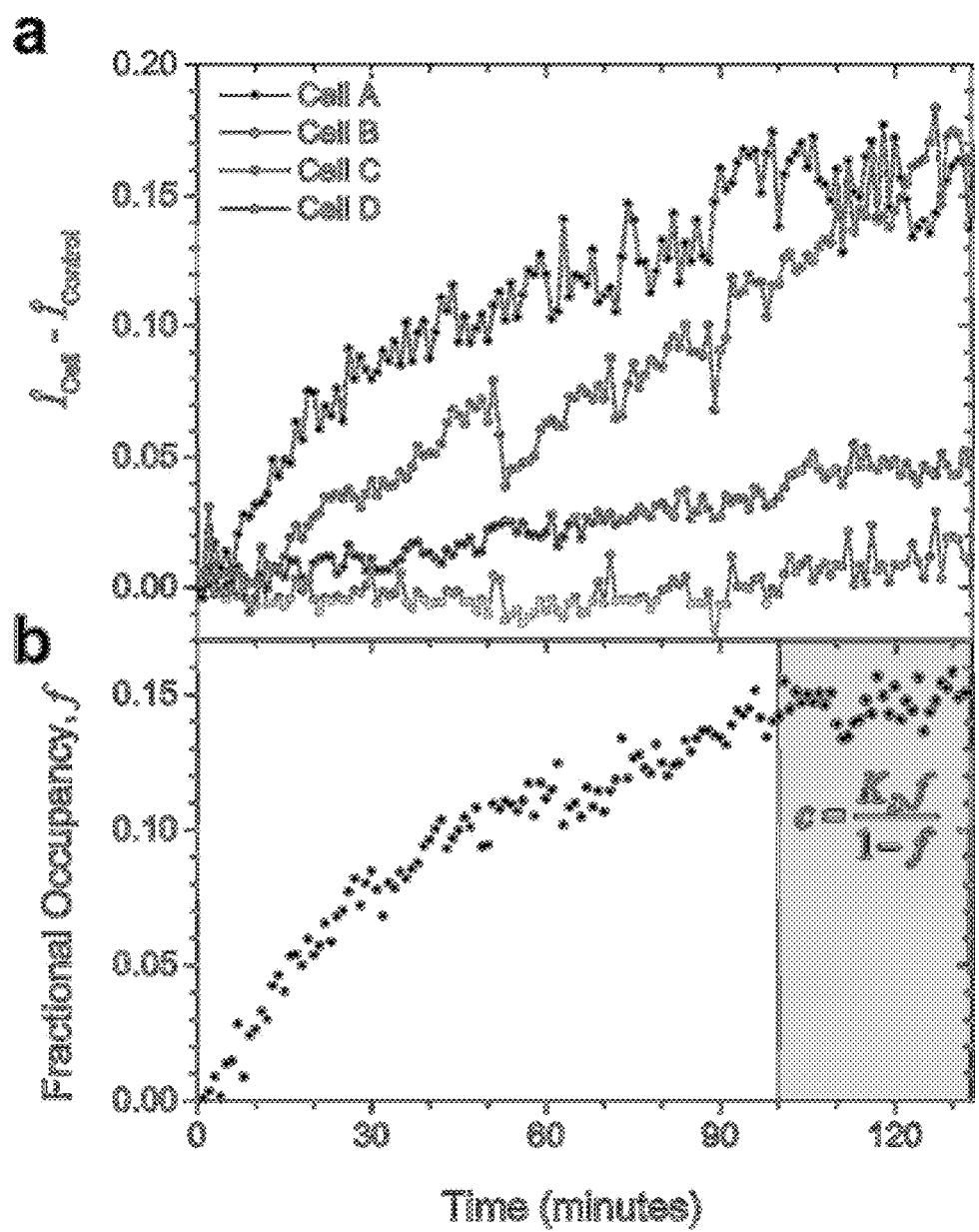
FIG. 4(a) shows a comparison of the time-dependent secretions from four single cell studies, all of which were within 15 µm of an array. The normalized LSPR image intensity of the array ($\hat{I}_{cell}$) minus the normalized intensity of a control array ($\hat{I}_{control}$) is plotted versus time.
FIG. 4(b) shows the fractional occupancy, f, of the array closest to Cell A as determined from the LSPR spectra which was collected simultaneously with the LSPR imagery. A concentration of 312±89 pM was calculated using the data in the period from 100 min to 135 min (highlighted region) at which f was constant with time.

From a collection of single cell measurements of this type, local concentrations were measured that varied from as high as a 312±89 pM about some cells to below the detection limit of the array for others (FIG. 4(a)). In each study, the cell was adjacent to the array with the center of the cell less than 15 μm from the array. The concentration at the array was calculated using $c(f)=K_D f/(1-f)$ where f is the fractional occupancy of surface-bound c-myc on the array determined from the simultaneously collected spectroscopic data of the LSPR peak response and $K_D$ is the equilibrium dissociation constant of 1.8 nM. The equation is valid if f is constant with time, a condition that was often applicable two to three hours into the measurement (FIG. 4(b)) and which is in agreement with FEA predictions that the concentration of antibodies surrounding a continuously secreting hybridoma cell closely approaches a steady state within 30 min of the cell being introduced to a new environment.

The experimental technique described herein enabled the quantitative spatio-temporal mapping of secreted proteins from one to three cells per experiment. As such, it stands as a complementary approach to high-throughput, single-cell immunosandwich assay techniques that measure hundreds or thousands of individual cells but with lower spatio-temporal resolutions. In addition, the chip architecture is designed to mimic that of a glass-bottomed culture dish setup. As such, polymer matrices (i.e. fibronectin, collagen) can be added to the substrate to enable adherent cell studies. We expect an amplified signal from cells resting on such a matrix and located directly over an array due to the trapping of the secreted proteins between the cell membrane and the substrate, thus allowing for the measurement of lower secretion rates. Many immunosandwich assays also incorporate multiplexing for the simultaneous detection of multiple analytes, which may be done by spot printing specific antigens to designated arrays. Finally, the label-free nature of LSPR imaging as well as its compatibility with TL and fluorescence imaging techniques gives experimental flexibility in that either modified or unmodified cells can be investigated.

Methods

Electron Beam Lithography of Au Nanostructures

The e-beam resists used for lithography were polymethyl methacrylate 4% in anisole (PMMA A4) and 6% ethyl lactate methyl methacrylate copolymer (MMA EL6), both from Microchem. The chromium etchant CR-7 was purchased from Cyantek and methyl isobutyl ketone (MIBK)+ isopropyl alcohol (IPA) in a 1:2 ratio was used for developing the resists. The substrates used for patterning the nanostructures were 25 mm diameter glass coverslips with a nominal thickness of 170 μm. The cleaning of the coverslips, deposition of a chromium thin film to prevent charging and spinning of the resist bilayer have all been previously described in Raphael et al., "A New Methodology for Quantitative LSPR Biosensing and Imaging," *Anal. Chem.*, 84, 1367-73 (2012). Samples were patterned via electron beam lithography using area doses in the range of 200 to 400 μC/cm$^2$. The samples were developed for 1 minute in an IPA/MIBK bath and the chromium layer wet-etched from the bottom of the pattern using the CR-7 etchant. A Ti/Au layer was deposited using a Temescal electron-beam evaporator. Following the metal deposition or etching, the PMMA/copolymer bilayer was removed by soaking in acetone for 4 hours.

Au Nanostructure Cleaning and Functionalization

The chip was cleaned by plasma ashing at 40 W in 300 mTorr of a 5% hydrogen, 95% argon mixture and then functionalized by immersion in a two-component ethanolic-based thiol solution (0.5 mM), consisting of a 3:1 ratio of SH—(CH$_2$)$_8$-EG$_3$-OH to SH—(CH$_2$)$_{11}$-EG$_3$-NH$_2$ for 18 hours (Prochimia). The SPN component of the SAM layer was first reacted with a 10 mg/mL solution of the heterobifunctional crosslinker sulfo-N-succinimidyl-4-formylbenzamide (Solulink) in PBS buffer (pH 7.4) and then conjugated to the c-myc peptide (HyNic-c-myc-tag, Solulink) in PBS buffer (pH 6.0) according to the manufacturer's instructions. Commercially obtained anti-c-myc antibodies (Genscript) were used for saturating the surface bound c-myc and normalizing array response at the end of each experiment.

LSPR, Transmitted Light, and Fluorescence Microscopy

All imagery was acquired using Zeiss AxioVision software, an inverted Zeiss Axio Observer microscope, and a thermoelectrically-cooled 16 bit CCD camera with 6.45×6.45 μm sized pixels (Hamamatsu ORCA R$^2$). Experiments utilized either a 63× oil immersion objective (FIGS. 1-3) or a 40× oil immersion objective (FIG. 4) and Koehler illumination. The camera was operated in 2×2 binning mode, giving image resolutions of 323 nm and 205 nm for the 40× and 63× objectives, respectively. CCD-based LSPR imaging and LSPR spectra were collected in a reflected light geometry using a 100 W halogen lamp for illumination and crossed-polarizers to reduce the background contribution from substrate-scattered light. Imagery and spectra were obtained simultaneously by placing a beam splitter at the output port of the microscope and a long-pass filter with a 593 nm cut-off wavelength was placed before the CCD camera. For the spectral measurements, the focused image of the entire nanostructure array was projected on to the end of a 600 μm diameter optical fiber and the spectra were subsequently measured with a spectrophotometer (Ocean Optics QE65000). Transmitted light illumination was obtained with the same configuration but using a 100 W halogen light source located above the chip. Fluorescence imagery was acquired using a 540-580 nm LED module (Zeiss Colibri) and a filter cube optimized for rhodamine fluorescence. Exposure times for LSPR imaging, transmitted light imaging, fluorescence imaging and spectra collection were 300 ms, 300 ms, 1 sec and 1 sec, respectively. TL images were contrast enhanced and false color was added to the grey-scale fluorescence images to better visualize the cell. All light sources were shuttered when data was not being acquired to minimize the possibility of phototoxic effects on the cells.

Microscope Incubation Environment and Stability

The microscope was equipped with a temperature controlled enclosure that kept the stage temperature at 37.0±0.04° C. (Zeiss). An additional incubation enclosure over the sample regulated the humidity and CO$_2$ content to 98% and 5%, respectively. Under these conditions, the drifts in the x, y and z directions were less than 3 nm/min. Focus drift was largely, though not entirely, corrected for during the experiment using a Zeiss Definite Focus System. In plane drift was corrected with commercially available post-experiment image alignment software (Zeiss Axio Vision).

Hybridoma Cell Culturing and Labeling

Hybridoma cells (clone 9E10, ATCC) were cultured in complete growth medium (RPMI-1640, ATCC) supplemented with 10% fetal bovine serum and 1% antibiotic/antimycotic (Sigma) using T75 flasks in a humidified tissue culture incubator at 37° C. under 5% CO$_2$ atmosphere. Cells were maintained at a density of 3-5×10$^5$ cells/mL and a subculture was performed every two days to maintain cell viability at 90-95%. Cell densities and viability were determined using a Countess automated cell counter (Invitrogen). Before being introduced on to the microscope, the cells were harvested in complete growth medium, counted and the viability was assessed. All cell preparations used for imaging had >92% viability. Cells were pelleted by centrifugation (3000 rpm×5 min), washed twice with RPMI-1640 SFM to remove secreted antibodies and adjusted to a cell density of 2×10$^6$ cells/mL. For imaging, 75 μL of cell solution was manually injected into the imaging chamber. After 5 minutes, typically 50-75 cells had adhered to the surface; the remaining cells were washed away with fresh SFM using the microfluidic perfusion setup. For fluorescence imaging, the plasma membrane of live cells was labeled with the membrane-localizing dye Lissamin rhodamine B 1,2-dihexadecanoyl-sn-glycero-3-phosphoethanolamine, triethylammonium salt (rhodamine DHPE) (Ex, 560 nm/Em, 580 nm) (L-RB, Invitrogen). The cells were washed and incubated for 20 min with 10 μM L-RB in Dulbecco' Modified Eagles Medium containing 25 mM HEPES (Invitrogen) on a rotating shaker at room temperature. Following incubation, cells were washed twice with SFM and prepared for imaging as described above.

Finite Element Analysis

Finite element analysis was conducted using FlexPDE software (version 5.0.8) assuming an 8 μm radius spherical cell with the bottom of the cell flattened to a 5.5 μm adhesion spot where it contacts the glass substrate.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A label-free method for the spatio-temporal mapping of secretions of anti-c-myc antibodies from individual cells in real time, comprising:
    using a chip for localized surface plasmon resonance (LSPR) imaging, comprising a glass coverslip compatible for use in a standard microscope and at least one array of functionalized plasmonic nanostructures patterned onto the glass coverslip, wherein the nanostructures were functionalized with a self-assembled monolayer comprising $SH-(CH_2)_8-EG_3-OH$ and $SH-(CH_2)_{11}-EG_3-NH_2$, and wherein the $SH-(CH_2)_{11}-EG_3-NH_2$ component was covalently conjugated with a c-myc peptide;
    placing at least one cell on the chip; and
    spatially and temporally mapping secretions of anti-c-myc antibodies from the cell using LSPR imaging.

2. The method of claim 1, additionally comprising simultaneously monitoring the cell secretions using transmitted light imaging, fluorescence imaging, or any combination thereof.

3. The method of claim 1, wherein the functionalized plasmonic nanostructures comprise gold nanostructures.

4. The method of claim 1, wherein the center of the cell of no more than 15 μm from an array.

5. The method of claim 1, additionally comprising normalizing each array individually.

6. The method of claim 1, additionally comprising using at least one array as a control array, wherein the control array is at least 65 μm away from the cell.

\* \* \* \* \*